United States Patent [19]

Hancock et al.

[11] 4,090,397
[45] May 23, 1978

[54] PNEUMATIC TRANSDUCER FOR UNDERGROUND BURIAL

[75] Inventors: George A. Hancock; Hugh W. McCutcheon, both of Seattle, Wash.

[73] Assignee: Slope Indicator Co., Seattle, Wash.

[21] Appl. No.: 810,262

[22] Filed: Jun. 27, 1977

[51] Int. Cl.² ............................................. G01N 33/24
[52] U.S. Cl. ............................................. 73/73; 73/716
[58] Field of Search ................. 73/73, 388 BN, 389, 73/406; 137/82, 83

[56] References Cited

U.S. PATENT DOCUMENTS

| | | | |
|---|---|---|---|
| 2,911,989 | 11/1959 | Neuhars | 137/82 |
| 3,388,598 | 6/1968 | Hall | 73/406 |
| 3,574,284 | 4/1971 | Thordarson | 73/406 |

*Primary Examiner*—S. Clement Swisher
*Attorney, Agent, or Firm*—Ford E. Smith

[57] ABSTRACT

A transducer for converting fluid pressure into pneumatic pressure for relay to a remote readout station comprises a valve body having a chamber spanned by a diaphragm which divides the chamber into a pore-fluid pressure cavity and a transducer cavity. The pore-fluid pressure cavity is in communication with fluid pressure in the environment surrounding the buried valve body. Three ducts communicate with the transducer cavity. The diaphragm carries a centrally located resilient hemisphere within the transducer cavity in axial alignment with only one of said ducts which constitutes a vent from said transducer cavity. During operation, rising gas pressure is applied at a known flow rate to said transducer cavity through one of said ducts, other than the venting duct, until the pressure in said transducer cavity exceeds the pre-fluid pressure against said diaphragm whereupon the hemisphere separates or is displaced from said venting duct and venting occurs with the attained pressure being read on the said remaining duct fixed to a suitable gage.

7 Claims, 6 Drawing Figures

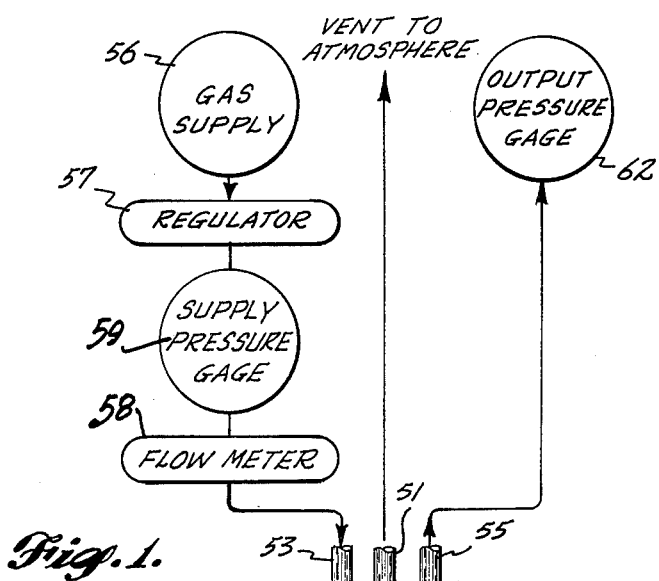
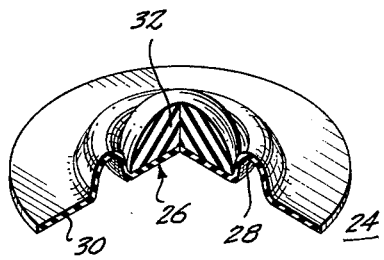
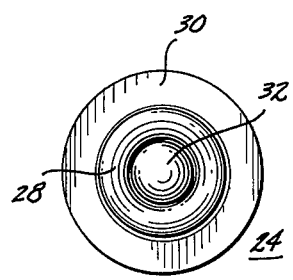
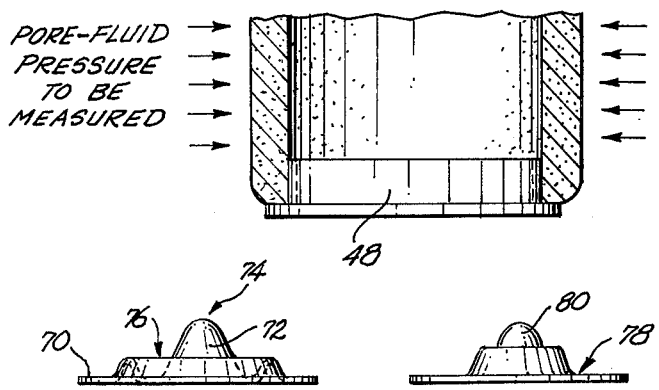

PNEUMATIC TRANSDUCER FOR UNDERGROUND BURIAL

PRIOR ART STATEMENT

Applicant' knowledge of prior art considered relevant to the instant invention, but nevertheless nonrelevant to singly or in combination defeat patentability, includes:

| U.S. Patents | | |
|---|---|---|
| 3,318,140 | 5/1967 | Shields |
| 3,365,949 | 1/1968 | Robinson |
| 3,388,598 | 6/1968 | Hall |
| 3,456,509 | 7/1969 | Thordarson I |
| 3,574,284 | 4/1971 | Thordarson II |
| 3,950,997 | 4/1976 | Hernandez |

PUBLICATIONS

Slope Indicator Co. — Model 51401 P/P. Transducer
Slope Indicator Co. — Model 56001 P/P. Transducer The various citations (copies supplied herewith) are nonrelevant for the several reasons stated below:

Shields is simply an early "bubbler"-type sensor of ground water pressure; Hall is a simple two-type diaphragm-type measuring device in which there is an imbalance of pressures when the diaphragm is actuated; Robinson is also a simple diaphragm-type sensor, likewise unbalanced when the diaphragm is actuated and is therefore nonlinear; Thordarson I illustrates the use of a pressure-sensitive diaphragm which is displaced by input pressure to permit a check valve to close, hence to interrupt gas flow and permit a reading to be taken; it includes intervening mechanical linkage; Thordarson II illustrates several diaphragm-actuated check valves interposed between inlet and outlet conduits in a transducer and appears to disclose more sophisticated apparatus of the type shown in Thordarson I; and Hernandez teaches a null balance sensor involving a bellows affected by the pore pressure and acting upon a common tire valve in a body having only two ducts.

The two publications show assignee's early two-tube transducers, in which Model 51401 has a diaphragm linked to a ball check valve, the diaphragm being responsive to pore pressure and being displaced by internal pressure buildup; and Model 56001 employs a diaphragm pressed to an O-ring centered in a flat surface. Air under pressure must flow across this surface to the center to derive a sensible reading. The Model 54020 transducer includes a hat-shaped rubber membrane which in a two-tube system is displaced by a swelling action of incoming gas to overcome the pore pressure. It obviously is not material to this case. All these transducers have been sold and used.

In addition to the foregoing, in a broader sense, transducers of the type here are disclosed and discussed to the extent deemed material to the subject matter of this application.

BACKGROUND OF THE INVENTION

Over the years civil engineers, in particular, and others, have become very sensitive to the necessity of monitoring pressures existing or developing underground in all manner of man's constructions. Such necessity has mothered a family of transducers useful to measure from a remote station pore pressures in the earth, differential pressures, and various hydraulic and pneumatic conditions underground and normally inaccessible. It is desirable that such measurements be made or data collected over long periods of time, years, in fact, so that progressive changes taking place underground may be evaluated and charted. Thus, primary characteristics required in such transducers are long-term stability, ruggedness, sensitivity, and repeatable accuracy. It is a prime object of this invention to provide a transducer that has such characteristics.

The art of transducers displays a wide variety of devices useful in underground measurement systems but which, for one reason or another, are less than fully satisfactory. Heretofore, pressure-actuated mechanical valves have been proposed without fully satisfying the need. Usually such valves include metal parts particularly subject to corrosion, tending to cause the transducers to malfunction. Other transducers have included diaphragm-shielded and diaphragm-actuated valve elements. These have in part been successful for a time, but it has been noted that their initial accuracy decays with the passage of time, due undoubtedly to wear and age. It has been another important object of this invention to provide a transducer of the diaphragm type which overcomes the earlier problems by avoiding the use of inherently inaccurate mechanical linkage means or probes for valve-actuating purposes.

It has been observed that many prior transducers that have suffered from the problems already mentioned have included a spring-pressed mechanical ball which must be unseated for proper functioning of the transducers. Springs are notoriously troublesome, especially in metallically unwholesome environments under compression for long periods of time and, where they are small, subject to fatigue and relatively non-linear in their functions. Thus, another object of this invention has been to produce a transducer that includes no metal springs or valve balls or metallic seats subject to the corrosive and debilitating effects of their underground environment. A still further object of this invention has been the provision of a rugged, inexpensive and compact transducer that can be easily manufactured wholly of inert and largely man-made synthetic materials not normally affected by oxidation, corrosion or fatigue.

The objects and advantages stated and others will become apparent during the course of the following detailed description of a preferred embodiment of this transducer invention.

SUMMARY OF THE INVENTION

The transducer herein disclosed comprises a chambered body in which a novel form of valve member is carried and moved by a circular, flexible diaphragm which divides and separates in a fluid-tight manner the internal chamber into a pressure cavity and a transducer cavity. Access for external fluid pressure into the body and the pressure cavity is supplied by a passage normally shielded by filter means operable to exclude all but the fluid. Communication to and from the transducer cavity is provided through three ducts, one located in the axis of the diaphragm and the other two spaced therefrom. The diaphragm carries in the transducer chamber a resilient body of hemispherical shape which, when fluid pressure acts in the pressure chamber on the diaphragm, is forced against the terminus of said axial duct to block passage of gas therethrough. Of the other two ducts, one is a gas supply duct and the other carries gas output under pressure to a gage which displays and records such pressure as the supply to the transducer cavity is increased or decreased. When gas pressure in the transducer cavity is great enough to displace the diaphragm and its flexible hemispherical surface against the counteracting environmental fluid pressure from the axial duct terminus, venting occurs through the axial duct. This event as a pressure drop can be read from the pressure gage in the system. The reading constitutes data useful in evaluating underground pressure conditions.

This device has a high degree of accuracy and linearity in operation because the relationship of the vent duct to the apex of the hemisphere causes an action of gas flow greater than or equal to the opposing pressure. When opposing pressures equalize, accuracy and linearity again are related and relayed by linkage of the output gage to the transducer chamber via an outlet duct, thus causing negligible deviation of accuracy regardless of the position of termination point to pneumatic transducer. There is no intervening mechanical linkage between the pressure being measured and the point at which the valve action takes place. Stated differently, the pore pressure acts directly on the underside of the diaphragm and forces its hemisphere into contact with the terminus of the vent duct for the advantage of accuracy and stability. This arrangement permits the inexpensive production of transducers of very small size, rugged and practically indestructible.

DESCRIPTION OF THE DRAWINGS

FIG. 1 is a longitudinal sectional view of a transducer according to this invention as associated with schematically shown control and read-out apparatus;

FIG. 2 is a perspective view of a diaphragm used in the transducer, portions being omitted for convenience of illustration;

FIG. 3 is a plan view of the diaphragm;

FIG. 4 is a cross-section on line 4—4 of FIG. 1;

FIGS. 5 and 6 are side elevation views of alternative forms of a transducer diaphragm.

DESCRIPTION OF A PREFERRED EMBODIMENT

The preferred form of this transducer comprises a valve body formed of a cuplike housing 10 and plug 12 which introduced and secured therein by matching threads 14. The inner bottom of cavity of housing 10 includes an annular shoulder 16 surrounding the central cavity 18. Shoulder 16 is grooved to receive O-ring 20 forming part of the system for peeling off chamber 21. A second O-ring 23 encircles the outer surface of plug 12 and seals with the inner wall of housing 10.

The resilient membrane or diaphragm 24 is formed of rubber or rubberlike materials such as a rubber-impregnated Dacron fabric with a central portion 26, a surrounding concavo-convex ridge 28, and a thin peripheral edge 30. See FIG. 2. On one side of central portion 26 is mounted the flexible or resilient hemisphere 32. It is preferred that hemisphere 32 and the convex surface of annular ridge 28 be on the same side of the diaphragm 24 as shown in FIG. 1. The diaphragm 24 is mounted in cup 10 so that its peripheral edge 30 is disposed between the annular shoulder 16 and the bottom edge of ring 17. O-ring 20 under diaphragm edge 30 forms a lower seal for the chamber 21. Ring 17 is forced into housing cup 10 to bear solidly on the edge 30 of the diaphragm 10 where it is secured as by adhesive between its outer face and the inner face of the cuplike recess in member 10.

Passage 40 extends axially downward from cavity 18 to chamber 42 in which a ring 44, equipped with a filter screen 45, may be threadedly secured. An elongated porous ceramic filter cylinder 46 is fitted in telescopic fashion to the lower exterior of cup 10. Cap 48 closes the lower end of filter cylinder 46.

Normally, plug 12 does not bear on ring 17, its bottom end being spaced from the ring to permit later adjustment of the space between the apex of hemisphere 32 and the passage it will control.

When the transducer, which will operate in any position, is buried in the earth, pore water under pressure penetrates filters 46 and 45, enters passages 42 and 40 to pore pressure cavity 18 where its force is applied to the underside of diaphragm 24. This pressure tends to distort the diaphragm 24 and displace the hemisphere 32 upward.

Plug 12 is drilled to provide the central duct 50 in axial alignment with the apex of hemisphere 32. When the hemisphere 32 is forced upward, it presses against and closes the lower terminus of duct 50, the same being designated the venting duct. Spaced apart in relation both to duct 50 and to each other are input duct 52 and output duct 54. The inner ends of ducts 52 and 54 are in open communication with transducer cavity 21. They are spaced away from duct 50 so that the hemisphere 32 has no action upon them when it is pressed upward. In FIGS. 1 and 4, the three ducts 50, 52 and 54 are shown as being disposed in a straight line intersecting the axis of plug 12. This is for convenience of illustration and not by way of limitation. It will be apparent that both ducts 52 and 54 can very well be on the same side of axial duct 50 in numerous arrangements so long as their terminii are spaced apart.

The ends of very small tubes 51, 53 and 55 are seated in plug 12 in communication with, respectively, ducts 50, 52 and 54. These conduit tubes, jacketed and formed into a bundle, extend to the ground surface at a station where they may be connected into the pressure indicator system. The supply side of the system shown schematically in FIG. 1 usually comprises a gas supply source 56, a regulator means 57, a supply pressure gage 59, and a flowmeter 58.

Axial tube 51 vents directly to the atmosphere.

Pressure tube 55 extends to output or readout pressure gage 62 where a reading of the counter pressure applied to chamber 21 and the upper side of the diaphragm 24 can be made when the force of the underground fluid pressure is equalled or exceeded. Excess pressure is then vented to atmosphere through orifice 50 and vent tube 51.

When the transducer body cup 10, plug 12 with diaphragm 24 in place, has been assembled as shown, it is inserted and tightly secured in jacket tube 64 with conduit tubes 51, 53 and 55 applied to the plug. Waterproof resinous potting material 60 is poured into tube 64 to embed and seal the ends of the conduits, casing tube 64, and the upper part of the transducer against exposure to and the intrusion of water.

The preferred material for forming hemisphere 32 is 90 D Buna "N" rubber, which may also be used for the membrane or diaphragm 24 by impregnating a high-strength Dacron fabric. Tubes 51, 53 and 55 are preferably of nylon, and their ends are tightly secured to plug 12 by an epoxy adhesive/sealant compound.

The dimensions and specifications of a preferred transducer are:

Diameter — CA 1.5 inches

Over-all length — CA 10 inches, including stone filter
  Diaphragm diameter — 0.625 inches
  Hemisphere diameter — 0.125 inches
  Travel of hemisphere — 0.019 inch
  Effective area of diaphragm — 0.07 square inch
  Volume of pressure cavity — 0.022 cc.
  Less than 0.022 cc. of water is displaced by the diaphragm during operation.
  Calibration offset — less than ± 0.3 psi.
  Sensitivity — less than ± 0.25 in. water
  Pressure range — 0–300 psi
  Diaphragm displacement — less than 0.02 cc. water
  Material for cup 10 and plug 12 — Polyvinyl Chloride.

The diaphragm 24 is flexible and due to the concavo-convex ridge 28 has a rolling action when porewater pressure acts up on it. Diaphragm has negligible spring force. When the hemispherical valve 32 is displaced from closing the terminus of vent passage 50, the gas pressure being applied to chamber 21 will be in balance with the pore-water pressure being overcome.

The measurement may be repeated by reducing input pressure to a level just below the output at which point it will also begin to decrease. The input is increased again and the readings are repeated.

For many applications, the flow rate may be limited by visual observation to avoid reading error. With extremely accurate and sensitive readout pressure gauges, the flow condition is monitored with a floating ball flowmeter. With constant flow for each reading, the small error due to flow rate and possible operator error is eliminated.

Fluid-pressure measurements may be continuously monitored and recorded on moving chart or digital datalogging equipment. Output signals may be compared to preset threshold values and utilized to trigger alarm devices.

This transducer does not require in-place calibration and has negligible zero shifts or changes in sensitivity. It provides a non-ambiguous measurement which is a result of the unique pneumatic-hydraulic null-balance condition. Tubing lengths or sizes do not affect calibration because the diaphragm 24 has negligible spring rate. Thus the sensitivity of the transducer (the smallest change in pore-pressure that can be measured) is increased and the calibration offset is minimal. The application of this technique to measurement of pore-water pressure results in an economical, stable and sensitive device giving long-term repeatability for periodic measurement of fluctuating pressures. It is not necessary to refer to calibration curves at any time since the calibration factor is essentially 1 to 1. Three types of porous filters are available. The standard ceramic filter has large pore size (i.e., CA 60 microns) and low air-entry pressure. An optional small pore size (i.e. 1.5/2.2 microns) filter has high air-entry pressure and permits the measurement of water pressure whenever pore-gas pressure is also present. A stainless steel disc filter of about 50 micron pore size and formed of sintered stainless steel particles is used when a smaller diameter transducer is required.

APPLICATION AND INSTALLATION OF TRANSDUCER

The transducer will operate in any position. It can be installed in boreholes or pressed into the soil. Well-points attached to steel pipe can be pushed into the soil, and do not require drilled holes.

In most applications, the transducer is embedded in a specified volume of sand. This area is sealed off from other water-bearing areas with Bentonite pellets or cement grout. The nylon tubing may be embedded directly in trenches using sand backfill whenever necessary to prevent rocks or other sharp objects from damaging the tubing. In cases where large lateral or vertical deformations may develop, the tubing can be protected by an outer corrugated or armored conduit.

Tubing lengths may be changed as necessary to suit conditions and will not affect the calibration of the transducer.

In many construction projects, it is essential to monitor pore-water pressure in both soil and rock. The disclosed transducer will provide in-situ pore-pressure data economically and reliably in support of the following objectives:

Monitoring water-pressure changes in regard to stability of slopes.

Control during construction of embankments and dams.

Soil stabilization to determine seepage patterns in soil and rock.

Surcharging of compressible foundations.

Gauging of water table and hydrostatic pressures.

Pumping tests to determine permeability and transmissibility coefficients.

Measuring of pore-pressure subjected to static and dynamic transient loadings in, for example, evaluating liquefaction potential associated with earthquake accelerations.

Stability of tailings dams and solid disposal areas.

Alternate valve means are shown in FIGS. 5 and 6. In FIG. 5, the rolling diaphragm 70 supports the somewhat conical valve member 72 having at its apex the hemispherical portion 74. Valve member 72 is axially located on the diaphragm and is surrounded by the usual concavo-convex ridge 76. In FIG. 6 is shown a planar diaphragm 78 which omits the rolling feature and which carries the semispherical body 80.

Throughout this description, the valve member 32 is referred to as a "hemisphere." As shown in FIGS. 1 and 2, member 32 is one-half a sphere. It will be observed that it is only the apex of element 32 which functions to block access to a conduit terminus and that the remainder of body 32 comprises base or support for the functionally operable apex of hemispherical shape. In this respect, the operating surface of any member 32 or 74 or 80 need only be hemispheric, i.e., having in part the form of a hemisphere at the apex.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the legitimate and valid scope of the appended claims, appropriately interpreted in accordance with the doctrine of equivalents.

What is claimed is:

1. A pneumatic transducer for underground burial, comprising:
   a valve body containing a cylindrical chamber;
   a flexible, annular, imperforate diaphragm peripherally secured in fluid-tight manner within said chamber, said diaphragm spanning said chamber perpendicular to its longitudinal axis and defining thereby a pore-fluid pressure cavity and a separate contiguous transducer cavity;

a resilient hemispherical element axially located on said diaphragm within said transducer cavity;

a fluid pressure input duct means and a fluid pressure output duct means in said body, each of said duct means communicating with said transducer cavity in spaced-apart relation to each other and to the axis of said hemispherical element;

a third duct means in said body axial of said transducer chamber and in alignment with the apex of said hemispherical element, said third duct means forming a venting duct from said transducer cavity to the atmosphere, the cavity end of said venting duct being disposed in close proximity to the apex of said hemispherical element; and means forming an inlet passage for liquid under pressure into the pore pressure cavity of said body.

2. The pneumatic transducer according to claim 1 in which the inlet passage to said pore-fluid pressure cavity terminates symmetrically of said diaphragm.

3. The pneumatic transducer according to claim 1 in which the diaphragm is of the rolling type.

4. The pneumatic transducer according to claim 1 in which said diaphragm has a thin-wall, concavo-convex annular ridge surrounding said hemisphere.

5. The pneumatic transducer of claim 4 in which the concave side of said ridge is exposed to fluid under pressure entering said pore-fluid pressure cavity.

6. The pneumatic transducer of claim 1 in which means is included whereby the cavity end of the venting duct may move toward or away from the apex of said hemisphere.

7. A pneumatic transducer for underground burial, comprising:

a valve body having a chamber spanned by a rolling diaphragm dividing the chamber into a porepressure cavity and a transducer cavity;

a resilient hemisphere axially located on said diaphragm within said transducer cavity;

passage means placing said pore-fluid pressure cavity in communication with liquid under pressure in the environment surrounding said body when it is buried underground;

conduit means in said body forming a fluid pressure input duct and a fluid pressure output duct, each of the said two ducts communicating with said transducer cavity in spaced-apart relation to each other and to the axis of said hemisphere; and duct means in said body in axial alignment with and in close proximity to the apex of said hemisphere and forming a vent to the atmosphere from said transducer cavity, said hemisphere being operable under pressure in the pore-fluid pressure cavity to normally prevent venting of said transducer cavity until fluid pressure in said transducer cavity at least equals the pressure force against said diaphragm in said pore-fluid pressure cavity.

* * * * *